United States Patent [19]

Uick

[11] Patent Number: 5,019,376

[45] Date of Patent: May 28, 1991

[54] SPARKLING PEARLESCENT PERSONAL CARE COMPOSITIONS

[75] Inventor: Heidi J. Uick, Racine, Wis.

[73] Assignee: S. C. Johnson & Son, Inc., Racine, Wis.

[21] Appl. No.: 600,274

[22] Filed: Oct. 22, 1990

Related U.S. Application Data

[63] Continuation of Ser. No. 323,480, Mar. 13, 1989, abandoned.

[51] Int. Cl.$^5$ ............................................. A61K 7/075
[52] U.S. Cl. ...................................... 424/70; 252/357; 252/547; 252/DIG. 13; 514/938; 514/943
[58] Field of Search ................. 424/70; 252/DIG. 13, 252/357, 547; 514/938, 943

[56] References Cited

U.S. PATENT DOCUMENTS

| | | | |
|---|---|---|---|
| 2,968,628 | 1/1961 | Reed | 252/305 |
| 3,149,042 | 9/1964 | Habicht et al. | 424/70 |
| 3,155,591 | 11/1964 | Hilfer | 424/70 |
| 3,320,133 | 5/1967 | Suga et al. | 514/789 |
| 3,502,769 | 3/1970 | Fukuhara et al. | 424/63 |
| 3,590,122 | 6/1971 | Roberts et al. | 424/70 |
| 3,651,931 | 3/1972 | Hsiung | 222/94 |
| 4,007,261 | 2/1977 | Sorrentino et al. | 424/70 |
| 4,183,917 | 1/1980 | Iwao et al. | 424/70 |
| 4,201,766 | 5/1980 | Grollier et al. | 424/70 |
| 4,275,055 | 6/1981 | Nathtigal et al. | 424/70 |
| 4,278,657 | 7/1981 | Tezuka et al. | 424/63 |
| 4,345,080 | 8/1982 | Bolich, Jr. | 546/6 |
| 4,357,141 | 11/1982 | Grollier et al. | 8/406 |
| 4,374,125 | 2/1983 | Newell et al. | 424/70 |
| 4,421,740 | 12/1983 | Burton | 424/70 |
| 4,438,096 | 3/1984 | Preston | 424/70 |
| 4,478,853 | 10/1984 | Chaussee | 514/772 |
| 4,493,824 | 1/1985 | Abe | 424/70 |
| 4,507,279 | 3/1985 | Okuyama et al. | 424/63 |
| 4,551,330 | 11/1985 | Wagman et al. | 424/59 |
| 4,608,392 | 8/1986 | Jacquet et al. | 514/844 |
| 4,614,200 | 9/1986 | Hsiung et al. | 132/202 |
| 4,654,207 | 3/1987 | Preston | 424/70 |
| 4,710,322 | 10/1987 | Dixon et al. | 424/70 |
| 4,777,039 | 10/1988 | Lang et al. | 424/70 |
| 4,824,594 | 6/1989 | Hoeffkes et al. | 252/174.21 |

Primary Examiner—Thurman Page
Assistant Examiner—Amy Hulina

[57] ABSTRACT

This invention relates to cationic oil-in water emulsion compositions which are especially useful as hair conditioning compositions which have a sparkling pearlescent appearance due to the presence of irregular platelet-like crystals suspended in the composition. The compositions comprise a cationic water-in-oil emulsion of from (a) about 0.1% to 5%, preferably from 0.1 to 0.8%, of a quaternary ammonium compound such as stearyl dimethyl benzyl ammonium chloride; (b) about 1–10%, preferably 1–2%, of a fatty acid having 12–16 carbon atoms such as myristic acid and a fatty monoalcohol having from 12 to 18 carbon atoms such as cetyl alcohol in a 70:30 to 95:5, preferably 75;25 to 85:15, weight ratio of acid to alcohol; (c) about 0.5–2% of a compatible thickening agent such as hydroxyethyl cellulose; optionally, up to bout 5% of additional cationic, nonionic and amphoteric surfactants; and the balance comprises water wherein the pH of the emulsion is from about 2–5, preferably from 2–4, and the viscosity is preferably from about 1,000 to 5,000 centipoise at 25° C.

8 Claims, 1 Drawing Sheet

SPARKLING PEARLESCENT PERSONAL CARE COMPOSITIONS

This is a continuation of co-pending application Ser. No. 07/323,480 filed on Mar. 13, 1989, now abandoned.

BACKGROUND OF THE INVENTION

1. Field of the Invention

This invention relates to personal care compositions such as hair conditioning compositions which are cationic water-in-oil emulsions which have a sparkling pearlescent appearance due to the presence of irregular platelet-like crystals.

2. Description of the Prior Art

Pearlescing agents are sometimes included in personal care compositions such as hair conditioners and shampoos to make them more attractive to the consumer. These conventional agents include ethylene glycol monostearate, ethylene glycol distearate, guanine, bismuth oxychloride on mica and the like. Suspended fish scales (guanine) can give a sparkling effect to such compositions, but are dependent on natural sources. U.S. Pat. No. 4,654,207 to Preston teaches a pearlescent shampoo where the pearlescing agent is a fatty acid ester like myristyl myristate or cetyl myristate which is added to the shampoo base from a substantially anhydrous solubilizing agent such as a surfactant. The pearlescent effect is observed after about 5 days waiting time which is unlike the direct use of myristyl myristate taught in Preston's earlier U.S. Pat. No. 4,438,096. Columns 1-2 of the '207 Patent further discuss the state of the art relative to pearlescing agents in cosmetic compositions.

FIG. 1 of this Specification is a photomicrograph at 400× magnification of a commercially available shampoo product sold by the Procter and Gamble Company under the name "PERT(®) Shampoo" which contains glycol distearate, i.e., ethylene glycol distearate. The pearlescing agent produces a uniform pearlescence to produce a shiny uniform sheen.

U.S. Pat. No. 3,320,133 to Suga et al. teaches a pearlescent face lotion. A phenol compound and a monohydric alcohol are said to be required to get floating pearlescent crystals of fatty acids in the lotion. Example 1 has 5 parts of stearic acid, 2 parts of linoleic/linolenic acid and 0.5 parts of decyl alcohol (93.3:7.7 ratio of fatty acid to fatty alcohol). Example 2 has no decyl or other fatty alcohol, but is said to be pearly. Example 3 has ethoxylated/propoxylated cetyl alcohol, but no other fatty alcohols. None of the examples contain quaternary ammonium salts, but all do contain significant amounts of alkanolamines to obtain a composition of weak alkalinity. This differs from my invention as will be explained further below.

U.S. Pat. No. 3,590,122 to Hutcheson et al. does not indicate that the conditioning shampoos it teaches are pearlescent. The product is composed of an organic synthetic detergent plus a saturated fatty acid like isostearic acid that is neutralized at least in part. Adjuvants such as fatty alcohols (e.g., cetyl alcohol or stearyl alcohol) can be present in an amount of up to 5% by weight, but the only reason for inclusion given is to "impart desired qualities".

A number of patents describe using fatty alcohols and fatty acids in hair conditioners and shampoos, some of which further contain fatty alkyl quaternary ammonium compounds:

| U.S. Pat. No. | Inventor | Comment |
| --- | --- | --- |
| 2,968,628 | Reed | Examples 3 and 11 |
| 3,149,042 | Habicht et al. | Example 4 |
| 3,502,769 | Fukuhara | Example 2 |
| 4,374,125 | Newell | Example 3, also has quaternary |
| 4,551,330 | Wagman et al. | Formula B has quaternary, cetyl alcohol and stearic acid (6/9.4 acid/alcohol) |
| 4,608,392 | Jacquet et al. | Examples 8, 15 and 16 have stearic acid/cetyl alcohol, highest is 75/25 |
| 4,614,200 | Hsiung et al. | Example 3 |
| 3,651,931 | Hsiung | Example 3 has 95.7/3.3 oleic acid/lauryl alcohol |
| 4,777,039 | Lang et al. | Pearlescent conditioner with quaternary plus fatty alcohol, no fatty acid |
| 4,357,141 | Grollier et al. | Hair dyes with polymeric quaternary plus fatty acid (oleic) and fatty alcohol (octyldodecyl) at 2/1 or lower acid/alcohol ratios |
| 4,201,766 | Grollier et al. | Polymeric quaternary, optionally has quaternary compound, Formulas 2g, 3c & 3g; col. 9 teaches fatty acids and fatty alcohols |

Further representing the state of the art are U.S. Pat. Nos. 3,155,591 (Hilfer); 4,007,261 (Sorrentino et al.); 4,278,657 (Tezuka et al.); 4,345,080 (Bolich); 4,421,740 (Burton); 4,478,853 (Chaussee); 4,493,824 (Abe); and 4,701,322 (Dixon et al.).

SUMMARY OF THE INVENTION

After studying the effects of including fatty acid in hair conditioning compositions which are cationic water-in-oil emulsions, I have found that the use of a relatively high ratio of certain fatty acids to certain fatty alcohols in the presence of certain fatty alkyl quaternary ammonium compounds unexpectedly results in a composition which has a sparkling pearlescent appearance which results in an attractive product. The sparkling nature of the compositions is due to the presence of irregular platelet-like crystals which tend to turn as the composition is poured or shaken. These crystals are illustrated in FIG. 2 of this Specification.

These compositions do not require the use of inorganic platelet-containing materials such as mica or fish scale type materials such as guanine.

These and other advantages are provided by a composition which comprises a cationic water-in-oil emulsion of from (a) about 0.1% to 5%, preferably from 0.1 to 0.8%, of a quaternary ammonium compound such as stearyl dimethyl benzyl ammonium chloride; (b) about 1-10%, preferably 1-2%, of a fatty acid having 12-16 carbon atoms such as myristic acid and a fatty monoalcohol having from 12 to 18 carbon atoms such as cetyl alcohol in a 70:30 to 95:5, preferably 75:25 to 85:15, weight ratio of acid to alcohol; (c) about 0.5-2% of a compatible thickening agent such as hydroxyethyl cellulose; optionally, up to about 5% of additional cationic, nonionic and amphoteric surfactants; and the balance water wherein the pH of the emulsion is from about 2-5, preferably from 2-4, the viscosity is preferably from about 1,000 to 5,000 centipoise at 25° C. wherein the composition contains irregular platelet-like crystals which impart a sparkling appearance to the composition.

DETAILED DESCRIPTION OF THE PRESENT INVENTION

This invention relates to a composition having a sparkling pearlescent appearance comprising a cationic oil-in-water emulsion of (a) from about 0.1% to 5% based on the total weight of the emulsion of at least one cationic surfactant selected from the group consisting of quaternary ammonium compounds of the formula $$[R^1R^2N^+R^3R^4]A^-;$$

$$[R^1R^2N^+(R^5)_2]A^-; \text{ and}$$

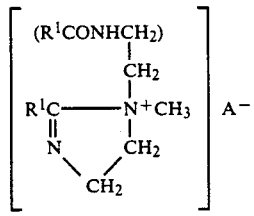

where $R^1$ is an alkyl group having an average of 8 to 23 carbon atoms, $R^2$ is an alkyl group of 1 to 4 carbon atoms, $R^3$ is $R^1$ or $R^2$, $R^4$ is $R^2$ or a benzyl group, $R^5$ is $(CH_2CH_2O)_nH$ where n is an integer of from 1 to 50, and A is an anion wherein the first formula does not include compounds where $R^2$, $R^3$ and $R^4$ each have from 1 to 4 carbon atoms;

(b) from about 1 to 10% by weight based on the total weight of the emulsion of
 (i) a fatty acid having an average of from 12 to 16 carbon atoms per molecule and
 (ii) a fatty monoalcohol having an average of from 12 to 18 carbon atoms per molecule
 in a 70:30 to 95:5 by weight ratio of (i) to (ii);

(c) from 0.5 to 2.0% by weight based on the total weight of the emulsion of a compatible thickening agent; and (d) the balance comprises water, wherein the pH of the emulsion is from about 2 to 5 and the composition contains irregular platelet-like crystals which provide the sparkling appearance.

Figure 1:
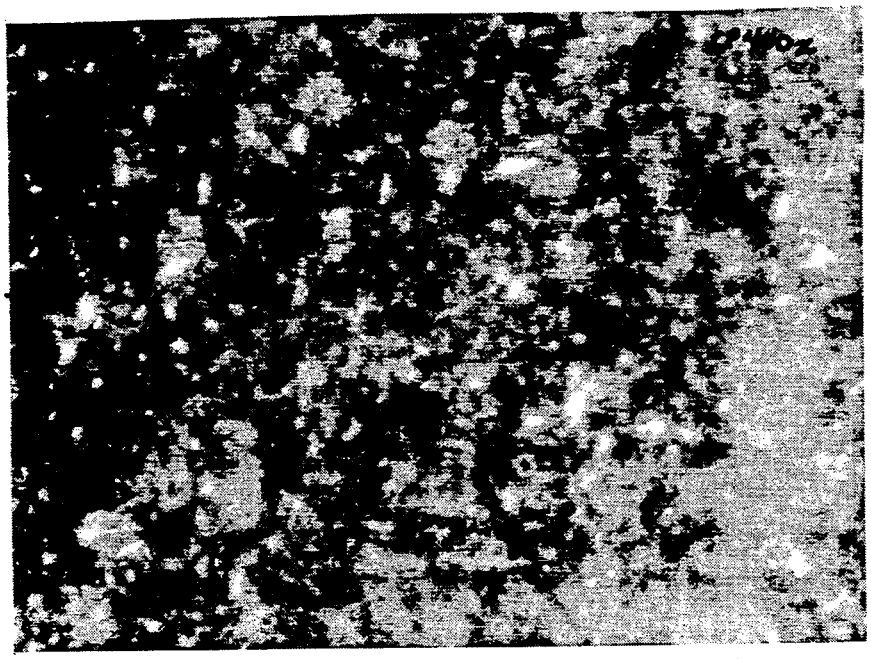
FIG. 1 is a photomicrograph using cross-polarized light at 400× magnification of a commercial pearlized shampoo composition.

The present compositions are characterized by the presence of irregular platelet-like crystals with shiny surfaces which provide a sparkling appearance. The irregularity causes the crystals to tumble in the emulsion and the platelet-like character causes the shiny surfaces to catch light and sparkle. These crystals do not plate out and form a uniform shine as is typical of many compositions containing pearlescing agents. FIG. 1 is a color photomicrograph at 400× magnification using cross-polarized lighting of a product formerly sold by Procter & Gamble Company as original "PERT(®) Shampoo for Normal & Dry Hair" which has a label ingredient statement as follows: Water, Sodium Laureth Sulfate, SD Alcohol 40, Cocamide MEA, Myristic Acid, Glycol Distearate, Fragrance, Disodium Phosphate, EDTA, Sodium Hydroxide, Imidazolidinyl Urea, Methylparaben, Propylparaben, D&C Green No. 8, and FD&C Blue No. 1. This anionic shampoo formulation appears to employ Glycol Distearate as the pearlizing agent and FIG. 1 shows that no signficant amount of large crystals are evident in the composition. The pearlescent agent apparently plates out and forms a uniform shiny, pearlescent surface.

Figure 2:
FIG. 2 is a photomicrograph at 400× magnification of the composition of the present invention showing the irregular platelet-like crystals responsible for the sparkling appearance of this composition.

FIG. 2 is a color photomicrograph at 400× magnification using cross-polarized lighting of a hair conditioning composition of the present invention which shows the presence of large crystals in various planes of rotation. Some surfaces of the crystals appear to be reflecting light towards the camera (i.e., towards the consumer's eye) while others are not. This alternating reflectance provides the sparkling appearance characteristic of these compositions. The irregularity of the crystals is also evident and this apparently prevents the crystals from plating out and forming a completely uniform pearlescence.

The compositions of the present invention are cationic water-in-oil emulsions which are especially useful as hair conditioning compositions. As such, they require the presence of at least one cationic surfactant in an amount of from 0.1% to 5% based on the total weight of the emulsion. More preferably, these surfactants comprise from about 0.1 to 0.8% of the emulsion composition and, most preferably from about 0.15 to 0.35% of the composition. I have found that certain such surfactants in the form of fatty alkyl quaternary ammonium compounds are necessary to cause the development of the crystals which provide the sparkling appearance noted above.

The required fatty alkyl quaternary ammonium surfactants are selected from the formulas noted as (a) above and are well known in the art, many of which are commercially available. Examples of surfactants of the formula $[R^1R^2N^+R^3R^4]A^-$ are those such as stearyl dimethyl benzyl ammonium chloride and lauryl dimethyl benzyl ammonium chloride, distearyl dimethyl ammonium chloride, dicoco dimethyl ammonium chloride and ditallow dimethyl ammonium chloride, and methyl tri(octyl-decyl) ammonium chloride which is sold under the tradename ADOGEN 464 by Sherex Chemical Company, Inc. of Dublin, Ohio (hereinafter "Sherex"). This formula excludes formulas where $R^2$, $R^3$ and $R^4$ each have from 1 to 4 carbon atoms. In these and the other formulas, A is an anion of the type conventionally used with quaternary ammonium compounds such as halides such as chloride and bromide, and alkyl sulfates such as methyl sulfate and ethyl sulfate, among others.

Examples of surfactants of the formula $[R^1R^2N^+(R^5)_2]A^-$ are ethyl bis(polyethoxyethanol)alkyl ammonium ethyl sulfate where the $R^1$ alkyl group has from 8 to 18 carbon atoms and the size of the alkyl group and the value of n in the $R^5$ groups are such that the average molecular weight of the compound is about 1110 (VARSTAT® 66 from Sherex), methyl bis(polyethoxy ethanol)alkyl ammonium chloride where the $R^1$ alkyl group has from 8 to 18 carbon atoms and the size of the alkyl group and the value of n in the $R^5$ groups are such that the average molecular weight of the compound is about 910 (VARIQUAT® K-1215 from Sherex), and methyl bis(2-hydroxyethyl)coco ammonium chloride (VARIQUAT 638 from Sherex).

Examples of the last formula listed under (a) above are those where $R^1$ has from 12 to 18 carbon atoms such as methyl-1-tallow amido ethyl-2-tallow imidazolinium-methyl sulfate (VARISOFT® 475 from Sherex) and methyl-1-oleyl amido ethyl-2-oleyl imidazolinium-methyl sulfate (VARISOFT® 3690 from Sherex).

Most preferred are quaternary ammonium compounds of the formula $[R^1R^2N+R^3R^4]A^-$ and, of these, preferably $R^1$ has an average of 18 carbon atoms, $R^2$ and $R^3$ are each alkyl groups having 1 carbon atom, $R^4$ is a benzyl group, and A is a chloride anion, i.e., stearyl dimethyl benzyl ammonium chloride.

Other surfactants which are compatible with the other ingredients present in the composition can be included such as conventional cationic, nonionic and amphoteric surfactants. The term "compatible" as used herein indicates that such ingredients do not cause the composition to become unstable or prevent the formation of the desired crystals to produce the sparkling effect. Preferably, no more than about 5% of such surfactants are included where a hair conditioning composition is desired and more preferably, no more than about 2% of additional compatible surfactants are present. These surfactants can be employed to improve the emulsion formed as well as to act as hair conditioners or anti-static agents, or to serve other beneficial purposes. Preferred additional surfactants are cationic surfactants such as fatty alkyl quaternary ammonium compounds and fatty amines which can be used for their hair conditioning properties.

Examples of such additional surfactants are quaternary ammonium compounds such as those of the formula $[R^1N+(R^2)_3]A^-$ where $R^1$, $R^2$ and A are as defined above and preferably, $R^2$ is a methyl group. These are exemplified by palmityl trimethyl ammonium chloride and coco trimethyl ammonium chloride. Other cationic surfactants can be fatty alkyl amines such as stearyl dimethyl amine. Examples of nonionic and amphoteric surfactants can be polyethoxylated fatty alcohols, fatty ethoxylated esters of sorbitol and fatty amine oxides.

Besides the required cationic surfactants of (a) above, two other required ingredients are a total of from about 1 to 10% by weight based on the total composition, preferably from about 1 to 2%, of (i) a fatty acid having an average of from 12 to 16 carbon atoms per molecule such as lauric acid, myristic acid and palmitic acid and (ii) a fatty monoalcohol having an average of from 12 to 18 carbon atoms per molecule such as lauryl alcohol, myristyl alcohol, cetyl alcohol and stearyl alcohol. Since fatty acids and alcohol are often derived from natural sources, there is generally a distribution of isomers present in the compositions and an average carbon chain length is often used.

To obtain the sparkling crystal appearance, the ratio of fatty acid to fatty alcohol must be from 70:30 to 95:5 and, more preferably, from 75:25 to 85:15 of acid to alcohol. Outside of these ratios, the crystals do not attain the structure necessary to cause a rather noticeable sparkling appearance due to the presence of irregular platelet-like crystals. Although stearic acid was observed to form small crystals which reflected some light, it was not found to produce compositions having this desirable appearance.

To keep the crystals in suspension and obtain the desired viscosity, preferably between about 1,000 and 5,000 centipoise at 25° C., from about 0.5 to 2% of a compatible conventional thickening agent of the type commonly used in cosmetic formulations is included in the compositions of the present invention. As used herein, "viscosity" refers to viscosity as measured on a Brookfield LV Viscosimeter using a #3 or #4 spindle, 30 r.p.m. for 30 seconds at 25° C. Examples of such thickeners are hydroxyethyl cellulose of the type sold under the tradename NATROSOL by Aqualon Company of Wilmington, Del. as well as hydroxypropyl cellulose and other nonionic or cationic water soluble and water dispersible thickening agents. The exact composition of the thickening agent or protective colloid is unimportant as long as it is cosmetically acceptable and compatible with the composition.

Water comprises the balance of the composition. Although tap water can be used if it contains relatively few ions, deionized water is preferred.

Adjustment of the pH of these compositions is done in a conventional manner using cosmetically acceptable organic or inorganic acids with organic acids such as citric acid being preferred. The pH of the cationic emulsions of the present invention is in the range of 2 to 5 and is more preferably in the range of 2 to 4.

As further additional ingredients, conventional additives such as perfumes, fragrances, dyes, proteins, solubilizing agents such as propylene glycol, and the like can be added to the composition in relatively small amounts provided that they are compatible with the compositions.

These compositions can be prepared in a manner similar to that employed for hair conditioning emulsions. U.S. Pat. No. 4,421,740 to Burton gives one procedure for accomplishing the same and refers to equipment that can be employed. The object is to form an emulsion composition which is then aged for about 5 days to a month or more at room temperature (about 20°-25° C.) to permit formation of the desired crystals in the composition.

Thus, the compositions of the present invention can be made by forming an intermediate composition which is generally about 25-30% of the total composition by mixing or dispersing together the cationic surfactant (a), any additional surfactant which may be used, the fatty acid, the fatty alcohol, pH adjusting agent, and sufficient water to permit the addition of 25-30 parts of this intermediate to 70-75 parts of additional ingredients to result in a total of 100 parts of the compositions of the present invention. The intermediate composition is heated to about 65°-72° C. to assist in blending the ingredients together. After the ingredients are well-mixed, the composition is then cooled to about 43° C. At this temperature, any perfumes to be used are added and dispersed into the intermediate composition. This cooled mixture is then homogenized at 500–8,000 p.s.i., preferably at about 4,000 p.s.i. Subsequent to the homogenization step, the intermediate is cooled back to about 25°-35° C.

In a separate vessel, the remaining water and any dyes and preservative to be added is heated to about 40°-45° C. with agitation and the thickening agent is added into the vessel with stirring. Stirring is continued until the thickening agent is hydrated and well-dispersed within the water. Any additional ingredients are then added with agitation to the vessel containing the hydrated thickening agent followed by 25-30 parts of the intermediate per 70-75 parts of the mixture in the vessel to make a total of 100 parts. Mixing is continued until a homogeneous composition is obtained. That composition is then aged at room temperature until such time as the composition has a sparkling pearlescent appearance due to the presence of irregular platelet-like crystals. Aging can take from about 5 days to one or more months. Aging can be conducted simply by packaging the composition in individual containers and storing the packaged compositions for a period of time.

The resulting compositions are especially suitable for use as ready to use hair conditioners or creme rinses which are applied directly to the hair of the user subsequent to shampooing.

The following examples are provided to show various aspects of the present invention without departing from the scope and spirit of the invention. Unless otherwise indicated, all parts and percentages used in the Examples are by weight.

EXAMPLE 1

This Example shows the preparation of a composition of the present invention which employs the preferred 80:20 ratio of myristic acid to cetyl alcohol and possessed a sparkling pearlescent appearance due to the presence of irregular platelet-like crystals. This is the composition shown in FIG. 2.

The intermediate had the following composition:

| Intermediate 1 | |
|---|---|
| Stearyl dimethyl benzyl ammonium chloride[1] | 1.34 |
| Cetyl alcohol | 0.938 |
| Myristic acid[2] | 3.752 |
| Cetyl trimethyl ammonium chloride[3] | 1.34 |
| Stearyl dimethyl amine[4] | 0.70 |
| Citric acid | 0.5075 |
| Deionized water | 90.5475 |
| Fragrance | 0.875 |
| Total | 100.00% |

[1]AMMONYX ® 4002 from Stepan Company of Northfield, IL, 94% active.
[2]EMERY 655 from Emery Division of Quantum Chemical Corp. of Cincinnati, OH.
[3]VARIQUAT ® E-228 from Sherex, 25% active.
[4]ADOGEN ® 342-D from Sherex.

The final composition had the following composition:

| Composition 1 | |
|---|---|
| Deionized water | 70.05 |
| Preservative[1] | 0.03 |
| Hydroxyethyl cellulose[2] | 0.75 |
| Collagen protein hydrolyzate[3] | 0.10 |
| Propylene glycol | 0.50 |
| Intermediate 1 | 28.57 |
| Total | 100.00% |

[1]KATHON ® CG solution from Rohm & Haas Co. of Philadelphia, PA which is 1.5% of 5-chloro-2-methyl-4-isothiazolin-3-one and 2-meth-4-isothiazolin-3-one.
[2]NATROSOL ® 250HHR from Aqualon.
[3]LEXEIN ® X250 from Inolex Chemicals Co. of Philadelphia, PA.

Intermediate 1 was prepared by mixing the ingredients in the order listed in a vessel with agitation followed by heating to 65°–71° C. and holding at that temperature for about 15 minutes. The mixture was cooled to 43° C., the fragrance was added and agitation was continued for another 10 minutes. Intermediate 1 was then homogenized in a Matin-Gaulin Homogenizer at 4,000 p.s.i. and held at 43° C. until it was used to prepare Composition 1.

Composition 1 was prepared by adding the preservative to the water in a vessel separate from the one containing Intermediate 1. The vessel contents were heated to 40°–43° C. with agitation and then the hydroxyethyl cellulose thickening agent was sifted into the agitating contents of the vessel. Agitation was continued until the thickening agent was fully hydrated and dispersed into the water. The protein and propylene glycol were then added while agitation was continued, followed by the addition of Intermediate 1. The composition was stirred an additional 15–30 minutes until it was homogeneous. Upon cooling to 25° C., the composition had a viscosity of 2,480 centipoise (#3 spindle, 30 r.p.m. for 30 seconds) and a pH of 2.65. After 51 days of storage at room temperature, Composition 1 has a pearlescent, sparkling appearance throughout the composition. A subsequent batch using this formulation was noted to exhibit a sparkling appearance within about 20 days after preparation of the batch.

EXAMPLE 2

In this Example, the formulation of Example 1 was modified by changing the ratio of myristic acid/cetyl alcohol to determine where compositions containing a sparkling pearlescent appearance would be obtained. Except for the changes in ratios, the formulations and procedures used to make them remained the same as in Example 1. In the listing below, only the amount of myristic acid and cetyl alcohol used in the Intermediate is listed.

| | | Intermediate | | | |
|---|---|---|---|---|---|
| Myristic Acid | Cetyl Alc. | Ratio | Viscosity | pH | Results |
| 0.00 | 4.69 | 0:100 | 5,960* | 3.0 | No platelets noted |
| 1.876 | 2.814 | 40:60 | 3,120 | 2.60 | No platelets noted |
| 2.814 | 1.876 | 60:40 | 2,276 | 2.65 | No platelets noted |
| 3.283 | 1.407 | 70:30 | 3,052 | 2.65 | Small crystal platelets observed after 15 weeks; no change after 10 months |
| 3.517 | 1.173 | 75:25 | 2,792 | 2.65 | Crystal platelets noted after 5.3 months. |
| 3.986 | 0.704 | 85:15 | 2,388 | 2.65 | Small crystal platelets seen after 7 days, obvious large platelets seen after 13 days |
| 4.221 | 0.469 | 90:10 | 2,824 | 2.55 | Crystal platelets noted after 6 days |
| 4.455 | 0.235 | 95:5 | 2,272 | 2.65 | Crystal platelets noted after 6 days, definite platelets: 9 months |
| 4.69 | 0.00 | 100:0 | 3,560 | 2.60 | Crystals noted after 6 days, no change after 10 months |

*Brookfield LV, spindle #4, 30 r.p.m. at 30 seconds, remainder are #3 spindle, 30 r.p.m. at 30 seconds, 25° C.

As shown above, no platelets were noted until a 70:30 ratio of myristic acid to cetyl alcohol was used and even then, the platelets were not as large or as prominent as in the compositions with 75:25 through 95:5 ratios. About the same results obtained for a 70:30 ratio were observed at a 100:0 ratio of myristic acid (i.e., no cetyl alcohol present) although some crystal platelets were noted in the 70:30 ratio composition. In these evaluations, "platelets" or "crystal platelets" is intended to mean a significant amount of irregular platelet-like crystals which gives a noticeable sparkling effect. In this and other Examples, "Crystals" indicates that slight sparkling was seen due to many small crystals, but was not nearly as noticeable upon the casual observation that a consumer would make as opposed to compositions containing "crystal platelets", the latter being the most desirable.

EXAMPLE 3

In this example, other types of fatty acids and fatty alcohols were substituted into the formulation used in Example 1 and prepared in the same manner. The types and amounts of these ingredients are reported below as well as the results of testing the compositions.

| Fatty Acid | Fatty Alc. | Ratio | Intermediate Viscosity | pH | Results |
|---|---|---|---|---|---|
| $C_{10}$: 3.752 | $C_{16}$: 0.938 | 80:20 | 720 | 2.40 | No platelets noted.* |
| $C_{12}$: 3.752 | $C_{16}$: 0.938 | 80:20 | 1,540 | 2.50 | A few platelets observed after 1 month, crystal platelets after 5 months. |
| 3.986 | 0.704 | 85:15 | 1,100 | 2.55 | A few platelets observed after 1 month, crystal platelets after 4 months. |
| $C_{16}$: 3.752 | $C_{16}$: 0.938 | 80:20 | 3,360 | 2.35 | Small platelets observed after 2 months, crystal platelets after 8 months. |
| 3.986 | 0.704 | 85:15 | 3,504 | 2.55 | Small platelets observed after 1 month, crystal platelets after 4.5 months. |
| 4.69 | 0.00 | 100:0 | 3,420 | 2.55 | No platelets observed. |
| $C_{18}$: 3.752 | $C_{16}$: 0.938 | 80:20 | 3,784 | 2.35 | Crystals observed after 2 months, no change after 9 months. |
| 3.986 | 0.704 | 85:15 | 3,768 | 2.55 | Very small platelets/crystals observed after 2.5 wks., no change after 4.5 months. |
| 4.69 | 0.00 | 100:0 | 2,560 | 2.50 | Very small platelets/crystals observed after 2 months., no change after 6.75 months. |
| $C_{14}$: 3.752 | $C_{12}$: 0.938 | 80:20 | 3,696 | 2.50 | Crystal platelets noted after 7 days. |
| $C_{14}$: 3.752 | $C_{14}$: 0.938 | 80:20 | 3,552 | 2.50 | Crystal platelets observed after 2.5 months. |
| 4.221 | 0.469 | 90:10 | 5,320** | 2.35 | Crystal platelets observed after 3.5 months. |
| $C_{14}$: 3.752 | $C_{18}$: 0.938 | 80:20 | 2,076 | 2.55 | A few platelets noted after 7 days, crystal platelets observed after 4 months. |

*Sample separated into 2 phases after 3 weeks.
**Brookfield LV, spindle #4, 30 r.p.m. at 30 seconds, remainder are #3 spindle, 30 r.p.m. at 30 seconds, 25° C.
Fatty acids:
$C_{10}$: Capric acid - EMERY 659 from Emery.
$C_{12}$: Lauric acid - EMERY 652 from Emery.
$C_{14}$: Palmitic Acid - EMERSOL 143 from Emery.
$C_{18}$: Stearic Acid - EMERSOL 153 from Emery.
Fatty Alcohols:
$C_{12}$: Lauryl alcohol - EPAL 12 from Ethyl Corp. of Baton Rouge, LA.
$C_{14}$: Myristyl alcohol - Lanette 14 from Henkel.
$C_{18}$: Stearyl Alcohol - ADOL ® 62 NF from Sherex.

Of the fatty acids tested, capric acid and stearic acid did not produce compositions containing the type of crystal platelets needed for the present invention. Use of palmitic acid without any fatty alcohol did not produce compositions containing the type of crystal platelets needed for the present invention. The three fatty alcohols tested all produced compositions containing the type of crystal platelets needed for the present invention in the ratios tested.

EXAMPLES 4–12

These Examples show the results of using different quaternary ammonium compounds or amounts thereof to produce compositions of the present invention. These compositions were prepared using the following formulations according to the procedure given in Example 1:

| Example No. | Intermediates 4 | 5 | 6 | 7 |
|---|---|---|---|---|
| AROSURF ® TA-100[1] | 1.696 | — | — | — |
| ADOGEN ® 464[2] | — | 1.876 | — | — |
| VARISOFT ® 475[3] | — | — | 2.098 | — |
| VARSTAT ® 66[4] | — | — | — | 2.214 |
| Cetyl alcohol | 0.938 | 0.938 | 0.938 | 0.938 |
| Myristic acid | 3.752 | 3.752 | 3.752 | 3.752 |
| ADOGEN ® 342-D | 0.700 | 0.700 | 0.700 | 0.700 |
| Citric acid | 0.5075 | 0.5075 | 0.5075 | 0.5075 |
| Deionized water | 91.5315 | 91.3515 | 91.1295 | 91.0135 |
| Fragrance | 0.875 | 0.875 | 0.875 | 0.875 |
| Total | 100% | 100% | 100% | 100% |

[1] Distearyl dimethyl ammonium chloride (94%) from Sherex.
[2] Methyl tri($C_8$—$C_{10}$) ammonium ethyl sulfate (85%) from Sherex.
[3] Methyl-1-tallow amido ethyl-2-tallow imidazolinium methyl sulfate (76%) from Sherex.
[4] Ethyl bis (polyethoxy ethanol) alkyl ammonium ethyl sulfate (72%) from Sherex.

| Example No. | Intermediates 8 | 9 | 10 | 11 |
|---|---|---|---|---|
| VARIQUAT K-1215[1] | 1.678 | — | — | — |
| AMMONYX ® 4002 | — | 1.696 | — | — |
| VARISOFT ® 110[2] | — | — | 2.126 | — |
| VARIQUAT E-228 | — | — | — | 6.378 |
| Cetyl alcohol | 0.938 | 0.938 | 0.938 | 0.938 |
| Myristic acid | 3.752 | 3.752 | 3.752 | 3.752 |
| ADOGEN ® 342-D | 0.700 | 0.700 | 0.700 | 0.700 |
| Citric acid | 0.5075 | 0.5075 | 0.5075 | 0.5075 |
| Deionized water | 91.5495 | 91.5315 | 91.1015 | 86.8495 |

-continued

| Example No. | Intermediates | | | |
|---|---|---|---|---|
| | 8 | 9 | 10 | 11 |
| Fragrance | 0.875 | 0.875 | 0.875 | 0.875 |
| Total | 100% | 100% | 100% | 100% |

[1] Methyl bis (polyethoxy ethanol) alkyl ammonium chloride (95%) from Sherex.
[2] Methyl bis (hydrogenated tallowamidoethyl) 2-hydroxyethyl ammonium methyl sulfate (75%) from Sherex.

To prepare the final compositions, the following formulation was used as in Example 1 where the intermediate employed corresponded to those described above: 70.05% deionized water, 0.03% KATHON® CG, 0.75% NATROSOL® 250HHR, 0.10% LEXEIN® X-250, 0.50% propylene glycol and 28.57% Intermediate (described above).

Example 12 was the same as Example 1, except the perfume, protein and propylene glycol components were not included. Thus, the Intermediate used to prepare Example 12 was as follows: 1.34% AMMONYX® 4002, 0.938% cetyl alcohol, 3.752% myristic acid, 1.34% VARIQUAT® E-228, 0.70% ADOGEN 342-D, 0.5075% citric acid and 91.4225% deionized water. This intermediate was homogenized at 3,000 p.s.i. due to an inability to obtain 4,000 p.s.i. pressure. The final composition for Example 12 had the formula: 70.65% deionized water, 0.03% KATHON® CG, 0.75% NATROSOL® 250HHR, and 28.57% Intermediate (described above).

Example 13 was similar to Example 12, but one half of the amount of the AMMONYX® 4002, VARIQUAT® E-228 and ADOGEN® 342D were used. Thus, the Intermediate used to prepare Example 13 was as follows: 0.67% AMMONYX® 4002, 0.938% cetyl alcohol, 3.752% myristic acid, 0.67% VARIQUAT® E-228, 0.35% ADOGEN 342-D, 0.5075% citric acid and 93.1125% deionized water. The final composition for Example 13 had the formula: 70.65% deionized water, 0.03% KATHON® CG, 0.75% NATROSOL® 250HHR, and 28.57% Intermediate (described above).

Example 14 was similar to Example 12, but the AMMONYX® 4002 and VARIQUAT® E-228 were eliminated from the formulation and only the ADOGEN® 342D was used. Thus, the Intermediate used to prepare Example 14 was as follows: 0.938% cetyl alcohol, 3.752% myristic acid, 0.70% ADOGEN 342-D, 0.5075% citric acid and 94.1025% deionized water. The final composition for Example 14 had the formula: 70.65% deionized water, 0.03% KATHON® CG, 0.75% NATROSOL® 250HHR, and 28.57% Intermediate (described above).

Example 15 was similar to Example 12, but the AMMONYX® 4002 was eliminated from the formulation. Thus, the Intermediate used to prepare Example 13 was as follows: 0.938% cetyl alcohol, 3.752% myristic acid, 1.34% VARIQUAT® E-228, 0.70% ADOGEN 342-D, 0.5075% citric acid and 92.7625% deionized water. The final composition for Example 13 had the formula: 70.65% deionized water, 0.03% KATHON® CG, 0.75% NATROSOL® 250HHR, and 28.57% Intermediate (described above).

The finished compositions were evaluated and the results were as follows:

| Ex. No. | Viscosity | pH | Results |
|---|---|---|---|
| 4 | 2,388 | 2.50 | Fine crystal platelets noted after 1.4 months. |
| 5 | 2,072 | 2.45 | Crystal platelets noted after 1.4 months. |
| 6 | 1,088 | 2.65 | Fine crystal platelets noted after 5 weeks. |
| 7 | 928 | 2.70 | Very fine crystal platelets noted after 5 weeks. |
| 8 | 1,484 | 2.80 | Very slight crystal platelet formation noted after 1 month. |
| 8 | 2,320 | 2.55 | Fine crystal platelets noted after 2.5 weeks, crystal platelets noted after 6 wks. |
| 10 | 3,124 | 2.75 | No platelets formed after 1 month. |
| 11 | 2,824 | 2.35 | No platelets formed after 2 months. |
| 12 | 1,984 | 2.45 | Crystal platelets noted after 3 weeks. |
| 13 | 2,724 | 2.40 | Crystal platelets noted after 1 month. |
| 14 | 2,368 | 2.65 | No platelets formed after 2 months. |
| 15 | 1,944 | 2.45 | No platelets formed after 2 months. |

Viscosity - Brookfield LV, #3 spirdle, 30 r.p.m. at 30 seconds, 25° C.

Examples 4–7, 12 and 13 formed or were appearing to form crystal platelets at the time of the last observation. At the last observation, Example 8 appeared to need more time to form crystal platelets. Examples 10, 11, 14 and 15 were comparative examples which did not form crystal platelets.

That which is claimed is:

1. A method of making a cationic oil-in-water emulsion having a sparkling pearlescent appearance comprising the steps of:
   I. blending
      (a) from about 0.1% to 5% based on the total weight of the emulsion of at least one cationic surfactant selected from the group consisting of quaternary ammonium compounds of the formula

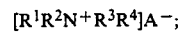

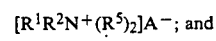

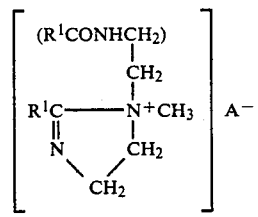

where $R^1$ is an alkyl group having an average of 8 to 23 carbon atoms, $R^2$ is an alkyl group of 1 to 4 carbon atoms, $R^3$ is $R^1$ or $R^2$, $R^4$ is $R^2$ or a benzyl group, $R^5$ is $(CH_2CH_2O)_nH$ where n is an integer of from 1 to 50, and A is an anion wherein the first formula does not include compounds where $R^2$, $R^3$ and $R^4$ each have from 1 to 4 carbon atoms;

(b) from about 1 to 10% by weight based on the total weight of the emulsion of
  (i) a fatty acid having an average of from 12 to 16 carbon atoms per molecule and
  (ii) a fatty monoalcohol having an average of from 12 to 18 carbon atoms per molecule
  in a 70:30 to 95:5 by weight ratio of (i) to (ii);
(c) an effective amount of a pH adjusting agent to obtain a pH of from about 2 to 5 in the emulsion; and
(d) a sufficient amount of water to obtain from 25 to 30 parts by weight of a first intermediate mixture;
II. homogenizing the first intermediate mixture;
III. separately mixing together
  (e) from, 0.5 to 2.0% by weight based on the total weight of the emulsion of a compatible thickening agent; and
  (f) a sufficient amount of water to obtain from 70 to 75 parts of a second intermediate mixture;
IV. mixing 25-30 parts of the first intermediate mixture with 70-75 parts of the second intermediate mixture together to obtain a total of 100 parts of the emulsion; and
V. aging the emulsion at room temperature until it contains irregular platelet crystals which provide a sparkling pearlescent appearance.

2. The method of claim 1 wherein the first intermediate mixture includes up to 5% of at least one additional compatible surfactant selected from the group consisting of cationic surfactants, nonionic surfactants and amphoteric surfactants.

3. The method of claim 1 wherein (b) is present in an amount of from about 1-2%, the ratio of (i) to (ii) is from 75:25 to 85:15, the fatty acid has an average of about 14 carbon atoms and the fatty alcohol has an average of about 16 carbon atoms per molecule.

4. A method of claim 1 wherein said (a) is $[R^1R^2N^+R^3R^4]A^-$ and is present in an amount of from about 0.1 to 0.8%.

5. The method of claim 4 wherein the composition contains up to about 2% by weight of at least one compatible cationic surfactant, has a pH in the range of from about 2 to 4 and has a viscosity at 25° C. of from 1,000 to 5,000 centipoise.

6. The method of claim 5 wherein (b) is present in an amount of from about 1-2% and the ratio of (i) to (ii) is from 75:25 to 85:15.

7. The method of claim 6 wherein the fatty acid has an average of about 14 carbon atoms and the fatty alcohol has an average of about 16 carbon atoms per molecule.

8. The method of claim 6 wherein said (a) is present in an amount of from about 0.15 to 0.35%, $R^1$ has an average of 18 carbon atoms, $R^2$ and $R^3$ are each alkyl groups having 1 carbon atom, $R^4$ is a benzyl group, and A is a chloride anion.

* * * * *

UNITED STATES PATENT AND TRADEMARK OFFICE
CERTIFICATE OF CORRECTION

PATENT NO. : 5,019,376

DATED : May 28, 1991

INVENTOR(S) : Heidi J. Uick

It is certified that error appears in the above-identified patent and that said Letters Patent is hereby corrected as shown below:

In the Abstract

Line 1: "oil-in water" should be --oil-in-water--.

Line 13: "75;25" should be --75:25--.

Line 16: "bout" should be --about--.

Signed and Sealed this

First Day of December, 1992

*Attest:*

DOUGLAS B. COMER

*Attesting Officer*     *Acting Commissioner of Patents and Trademarks*